(12) United States Patent
Yamamoto

(10) Patent No.: US 10,905,380 B2
(45) Date of Patent: Feb. 2, 2021

(54) SUBJECT-INFORMATION ACQUISITION APPARATUS

(71) Applicant: CANON KABUSHIKI KAISHA, Tokyo (JP)

(72) Inventor: Takeshi Yamamoto, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 1131 days.

(21) Appl. No.: 15/305,077

(22) PCT Filed: Apr. 20, 2015

(86) PCT No.: PCT/JP2015/002138
§ 371 (c)(1),
(2) Date: Oct. 18, 2016

(87) PCT Pub. No.: WO2015/162896
PCT Pub. Date: Oct. 29, 2015

(65) Prior Publication Data
US 2017/0035361 A1    Feb. 9, 2017

(30) Foreign Application Priority Data
Apr. 21, 2014   (JP) ................................ 2014-087467

(51) Int. Cl.
*A61B 5/00* (2006.01)

(52) U.S. Cl.
CPC ............ *A61B 5/708* (2013.01); *A61B 5/0095* (2013.01); *A61B 5/4312* (2013.01)

(58) Field of Classification Search
CPC ...... A61B 5/708; A61B 5/4312; A61B 5/0095
See application file for complete search history.

(56) References Cited

U.S. PATENT DOCUMENTS

| | | | |
|---|---|---|---|
| 6,409,668 B1 | 6/2002 | Wollschlaeger | |
| 7,264,592 B2 * | 9/2007 | Shehada | A61B 8/0825 128/915 |
| 2011/0306865 A1 | 12/2011 | Thornton et al. | |

FOREIGN PATENT DOCUMENTS

| | | |
|---|---|---|
| JP | 2007282960 A | 11/2007 |
| JP | 4341987 B2 | 10/2009 |
| JP | 2012-110551 A | 6/2012 |
| JP | 2012179348 A | 9/2012 |
| JP | 2013-128655 A | 7/2013 |
| WO | 9955234 A1 | 11/1999 |

\* cited by examiner

*Primary Examiner* — Joel Lamprecht
(74) *Attorney, Agent, or Firm* — Canon U.S.A., Inc. I.P. Division

(57) ABSTRACT

A blind area is reduced by reducing an area between a subject and a receiver in which acoustic waves do not propagate. The present invention relates to a subject-information acquisition apparatus including a base; a subject holding member on the base; a receiver including a plurality of transducers and a support member on which the plurality of transducers are disposed; and a fluid-level adjusting mechanism configured in such a manner that an acoustic matching material in a space enclosed by the base, the subject holding member, and the receiver can be at a fluid level higher than a boundary between the subject holding member and the base.

11 Claims, 12 Drawing Sheets

[Fig. 1]
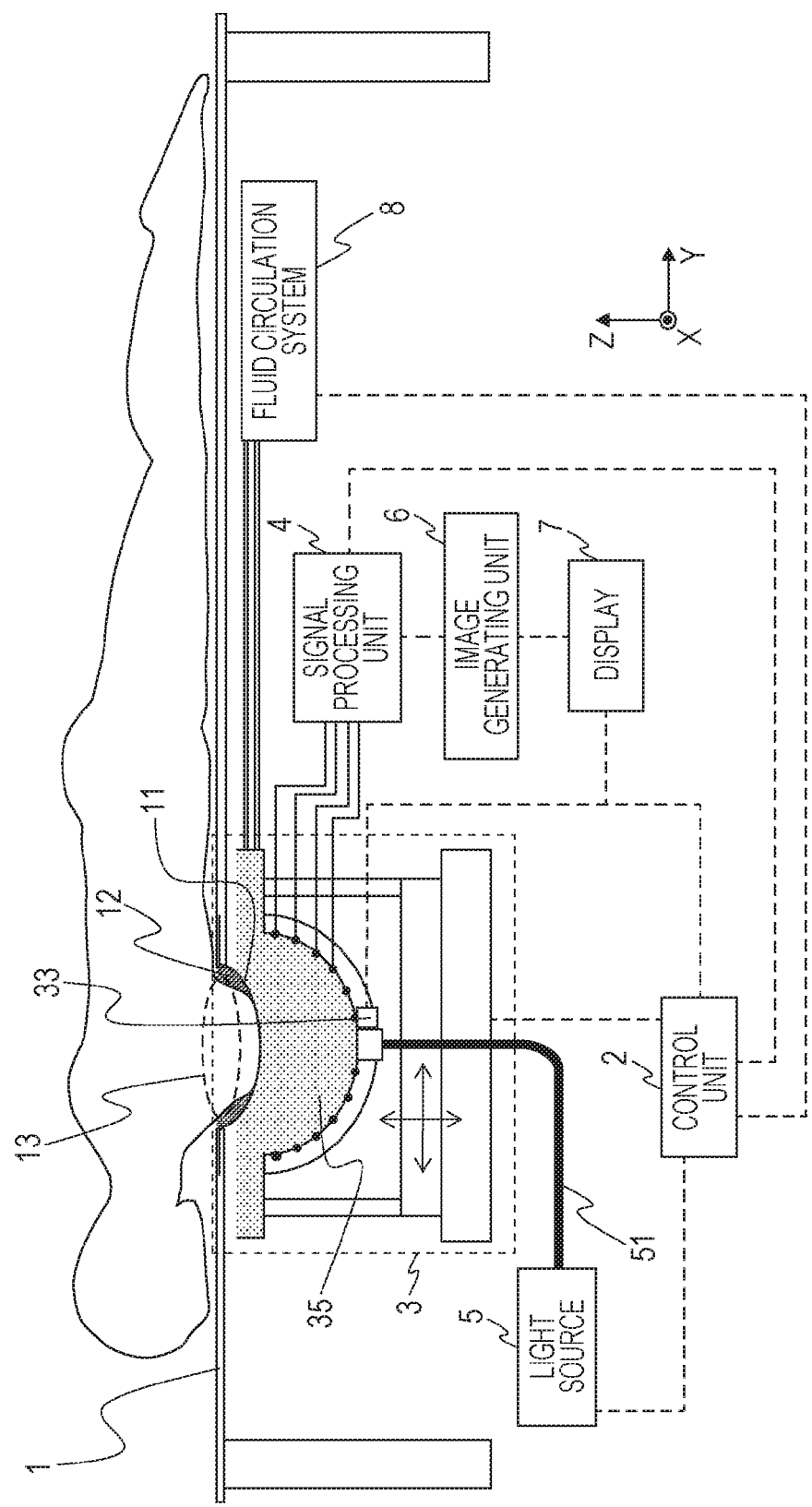

[Fig. 2]
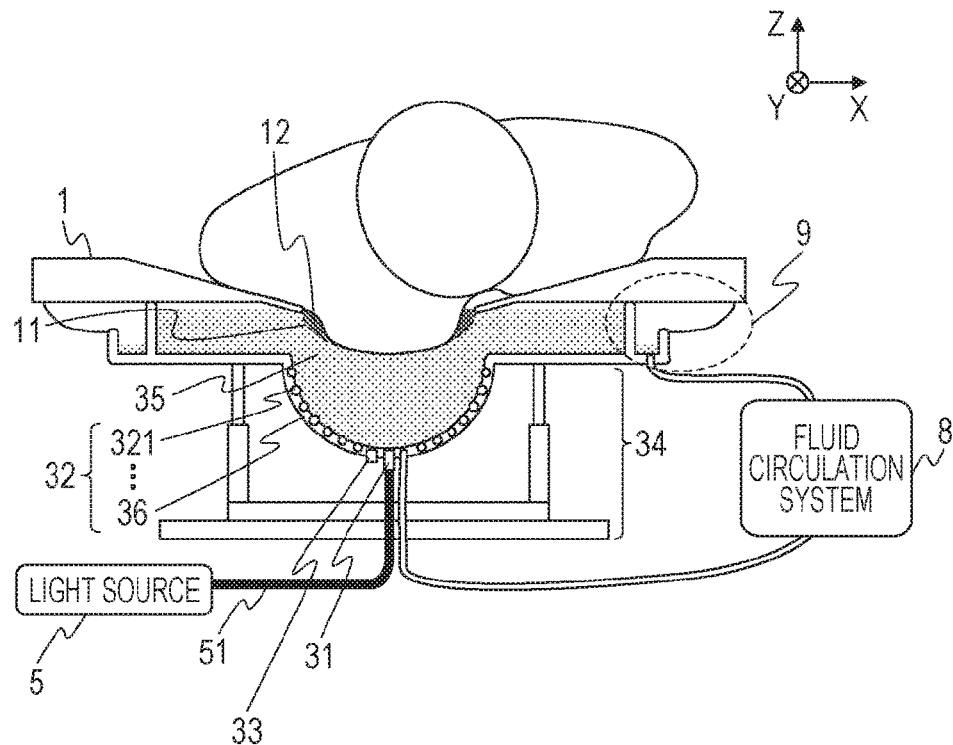
[Fig. 3]
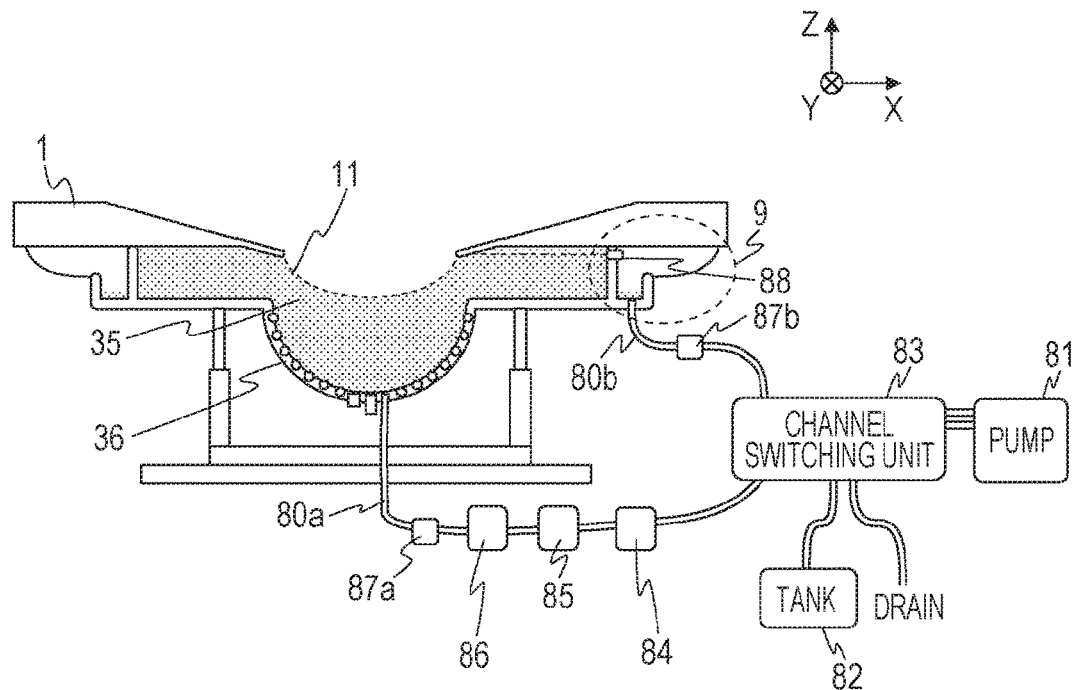

[Fig. 4]
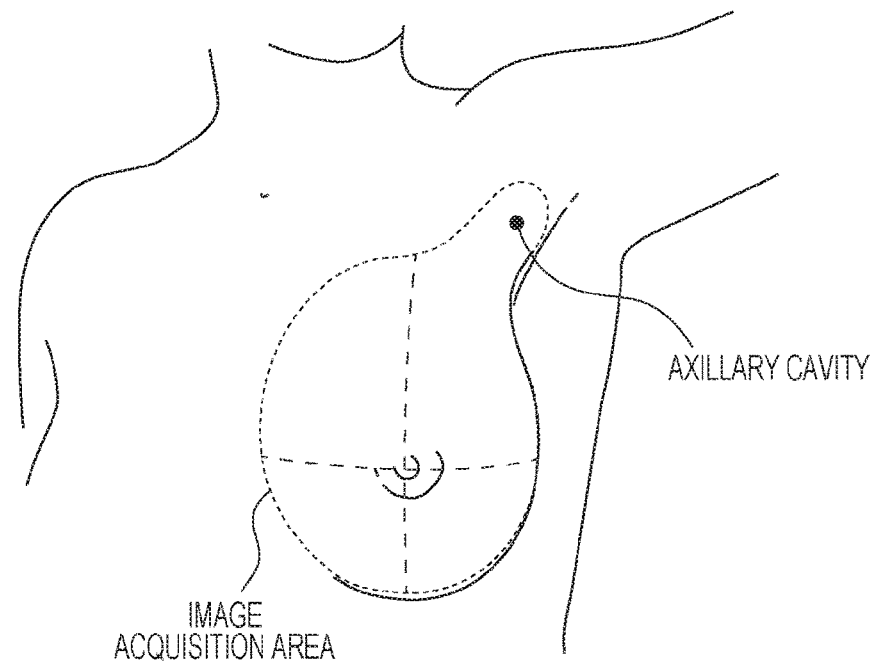
[Fig. 5A]
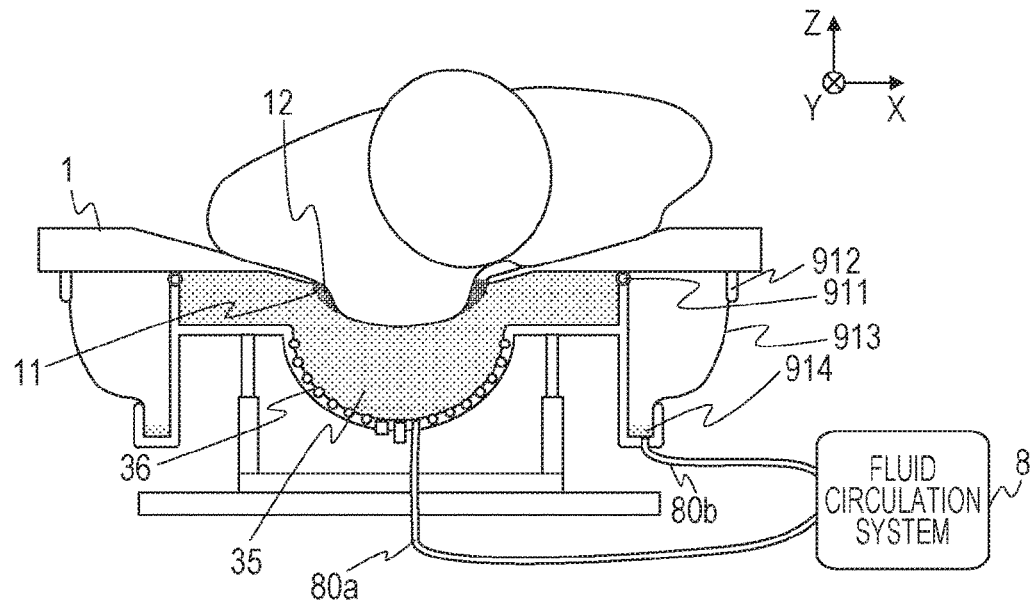

[Fig. 5B]
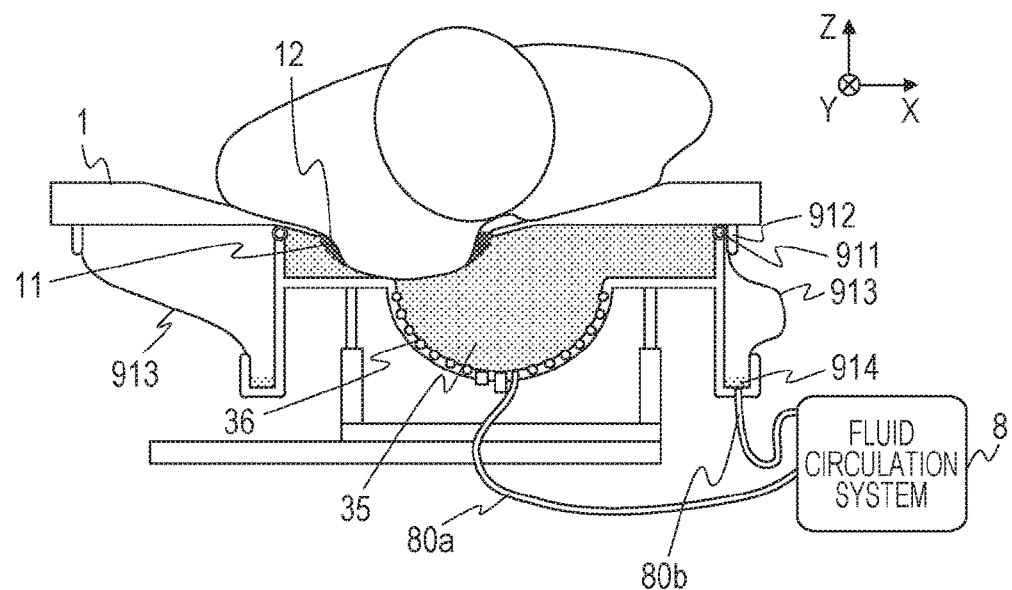
[Fig. 6A]
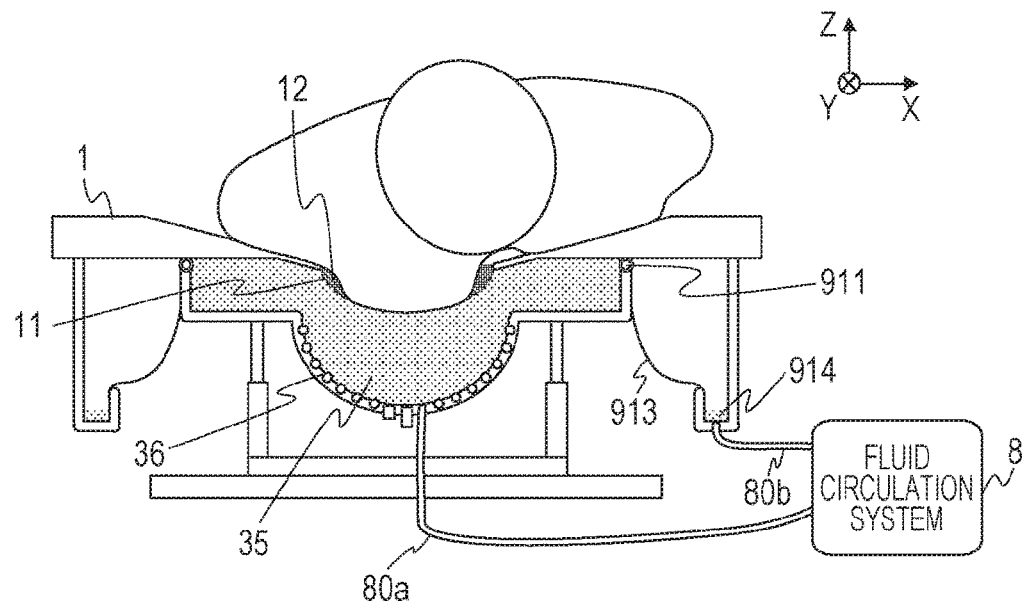

[Fig. 6B]
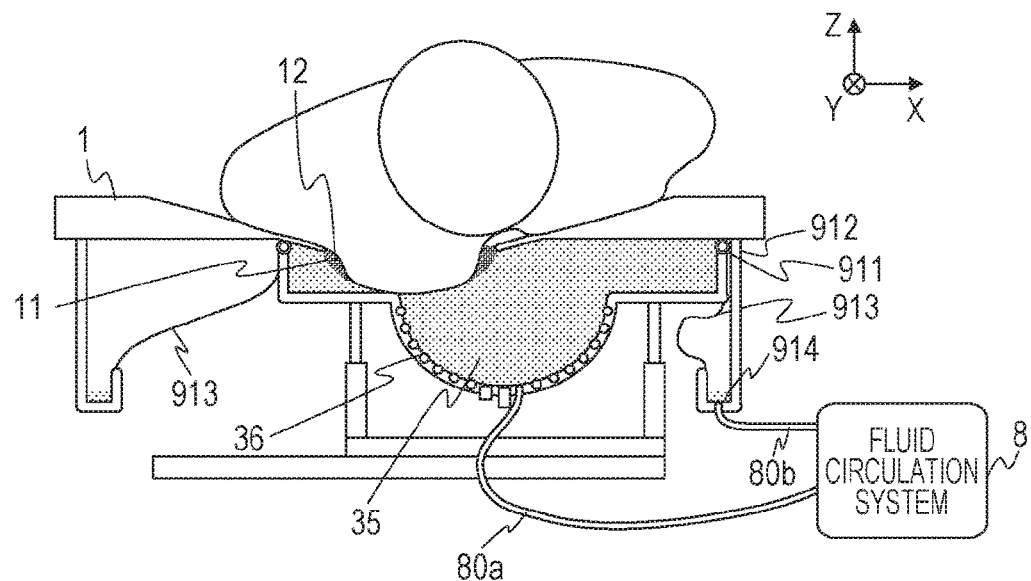
[Fig. 7A]
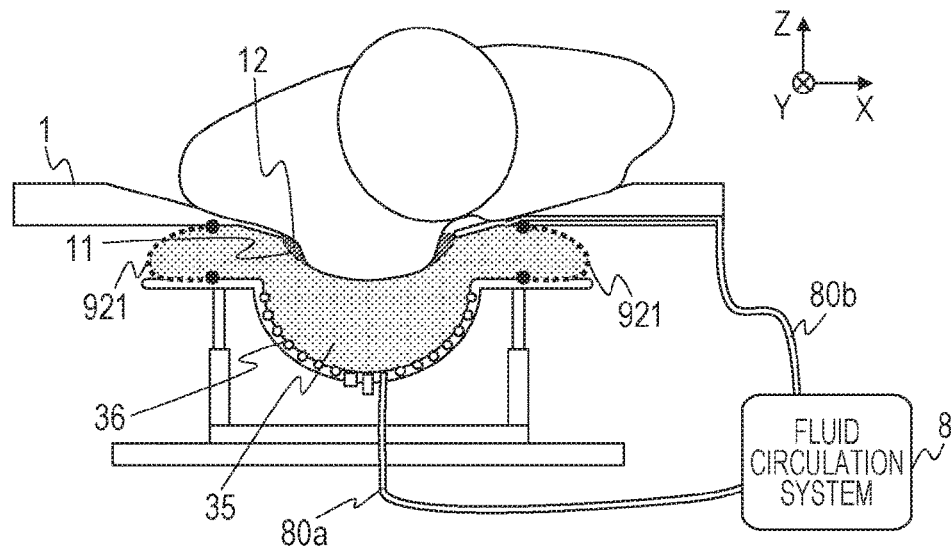

[Fig. 7B]
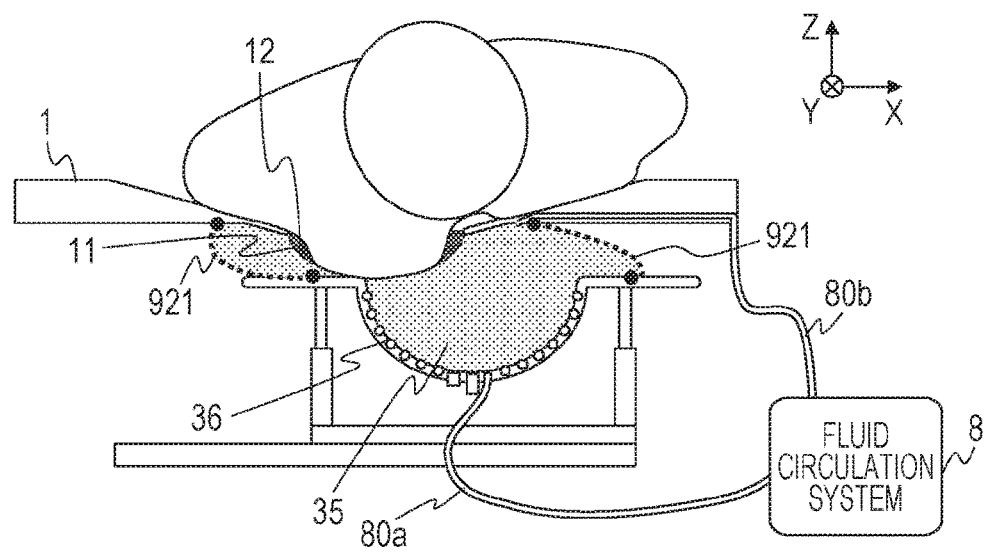
[Fig. 8A]
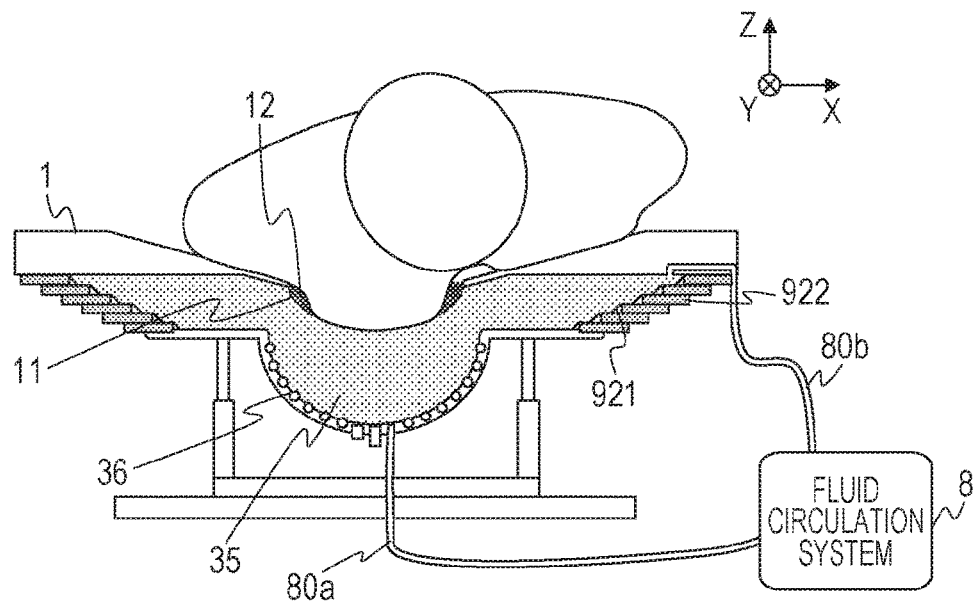

[Fig. 8B]
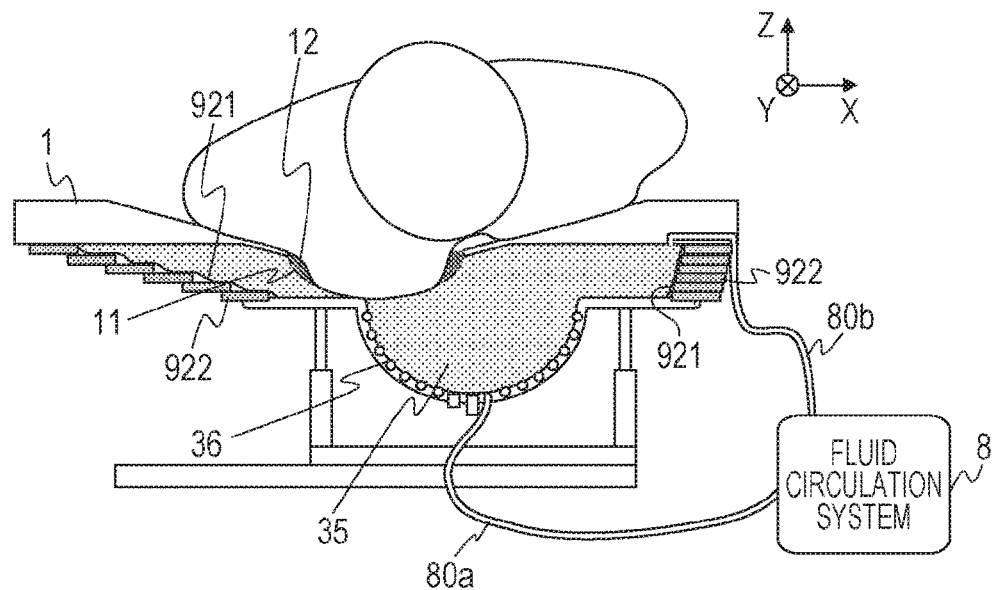
[Fig. 9A]
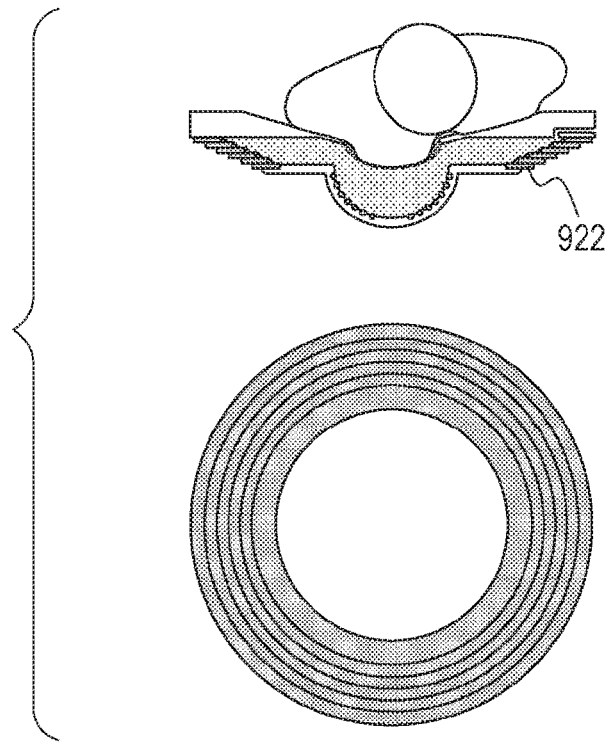

[Fig. 9B]
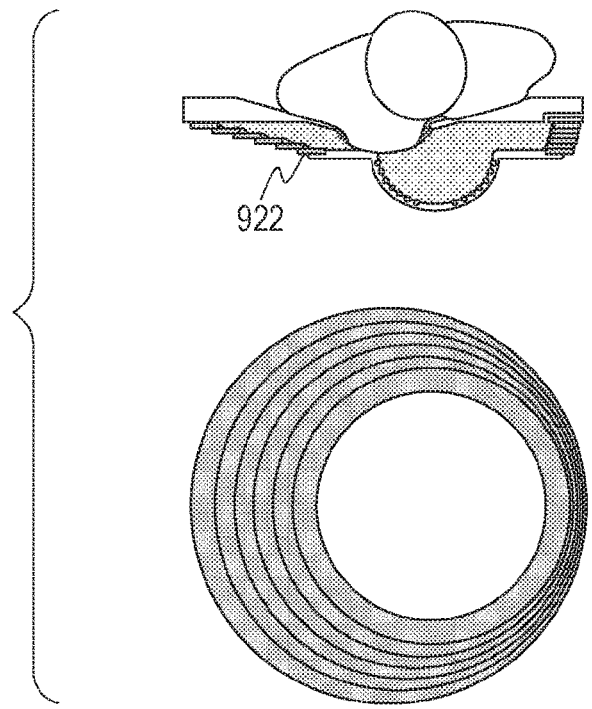
[Fig. 10A]
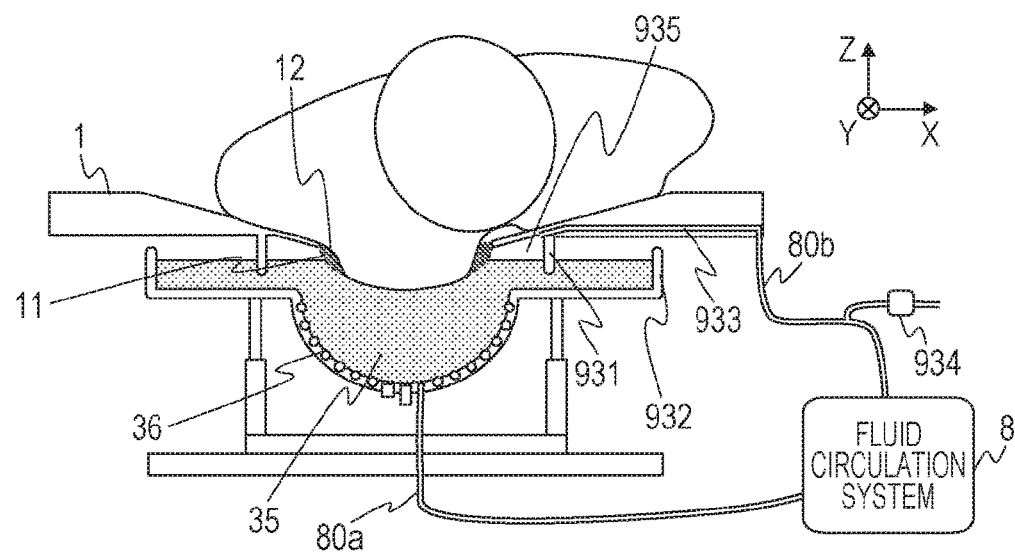

[Fig. 10B]
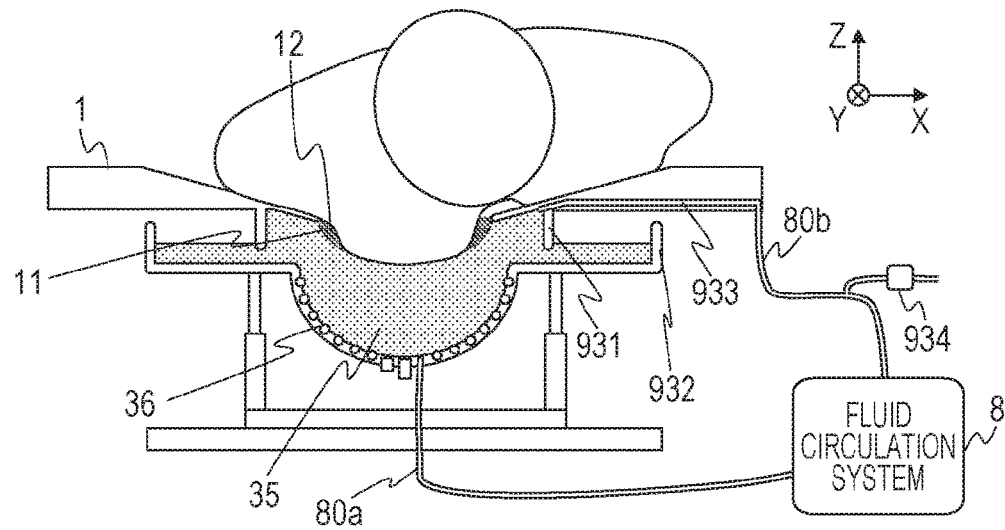
[Fig. 10C]
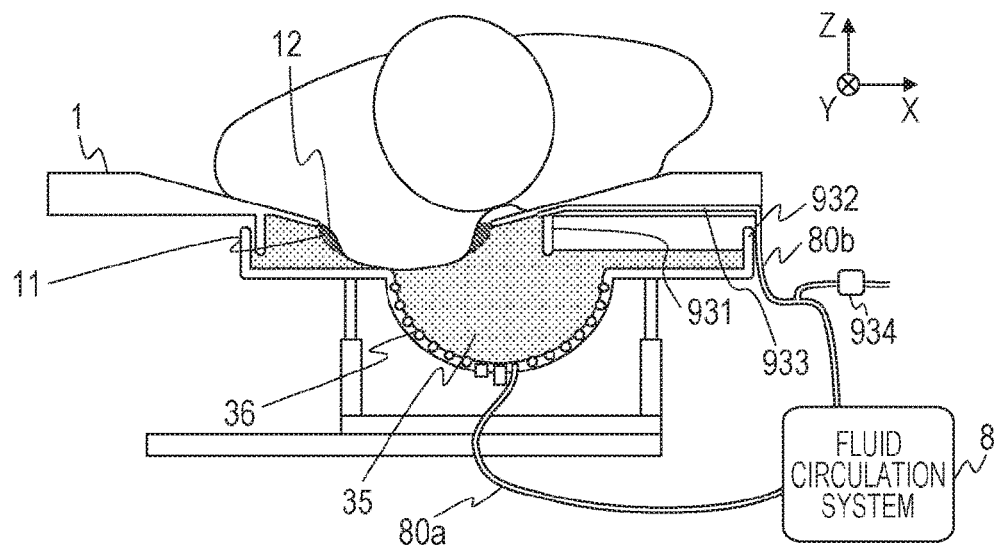

[Fig. 11A]
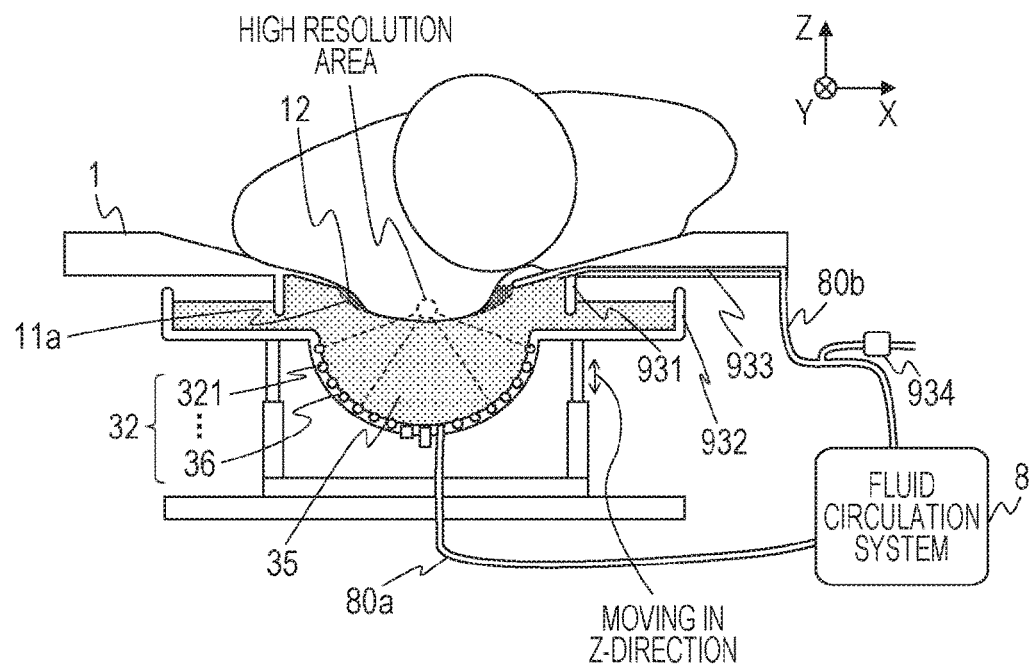
[Fig. 11B]
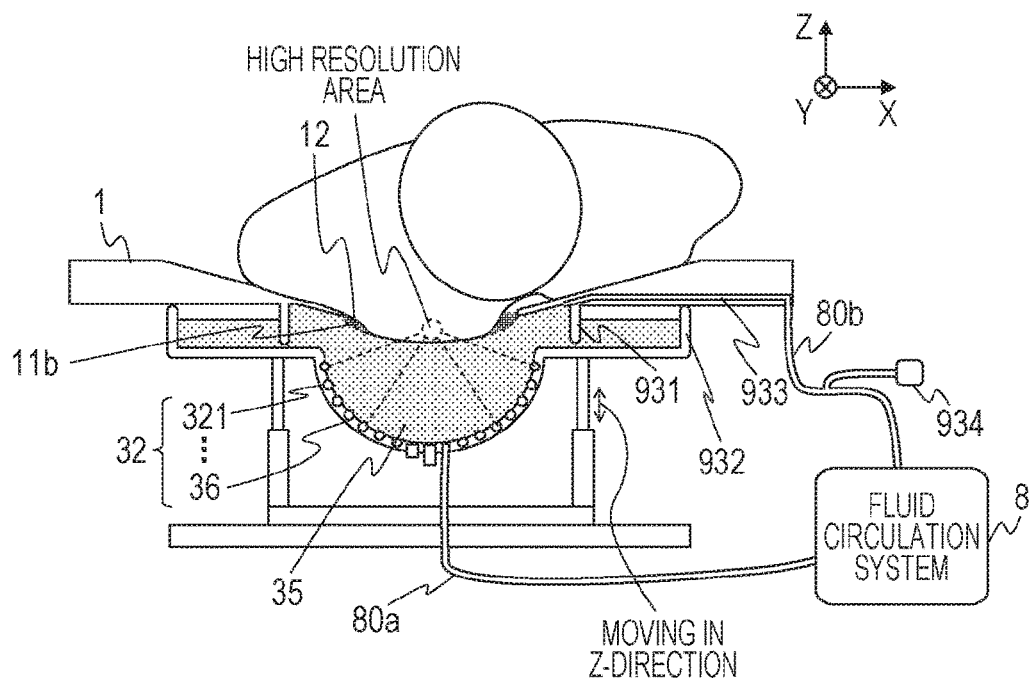

[Fig. 12A]
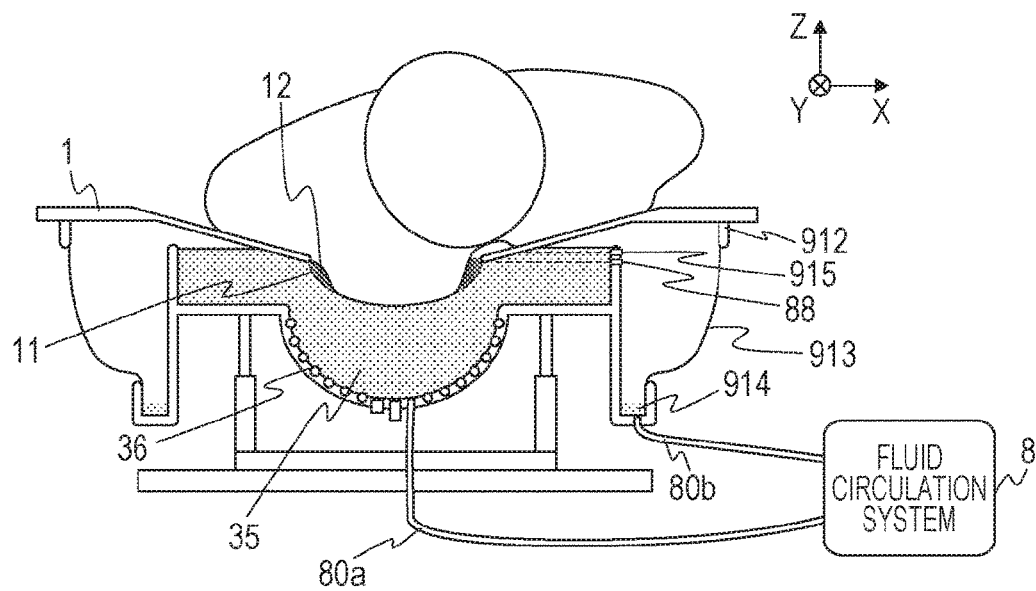
[Fig. 12B]
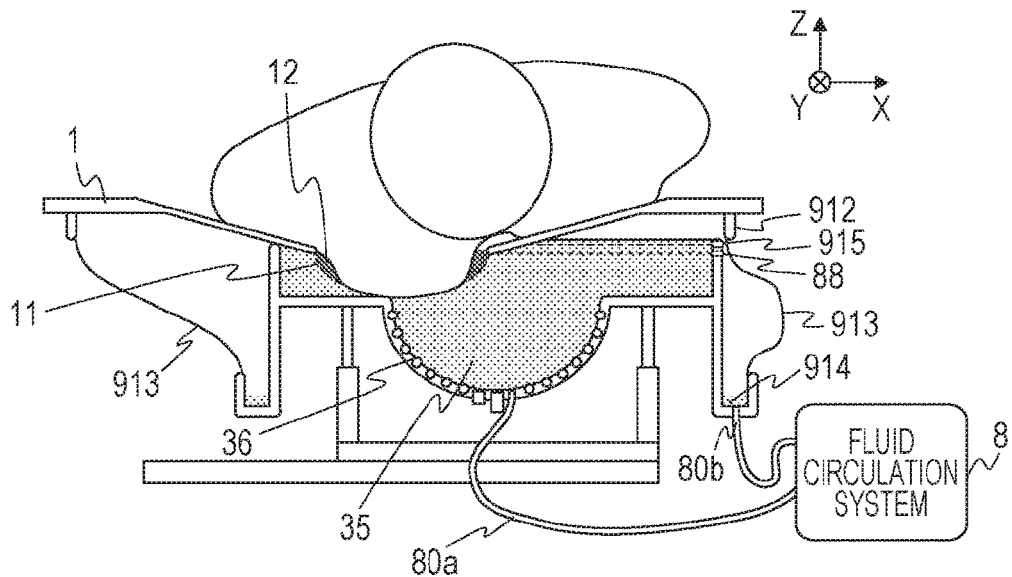

[Fig. 13]
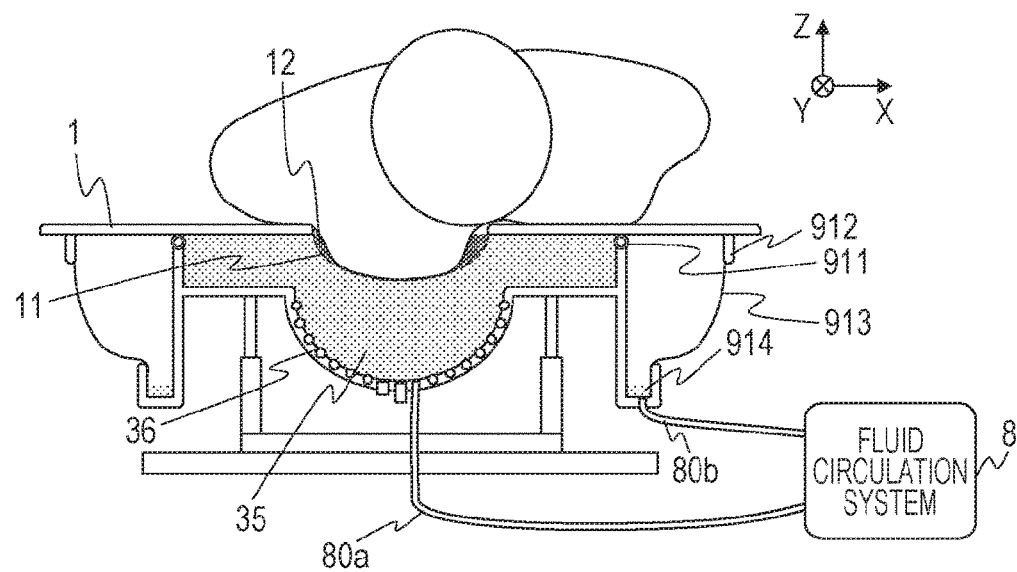

SUBJECT-INFORMATION ACQUISITION APPARATUS

TECHNICAL FIELD

The present invention relates to a subject-information acquisition apparatus, for example, a photoacoustic apparatus for use in observing the breast of a living organism.

BACKGROUND ART

In recent years, a photoacoustic imaging apparatus that images the interior of a living organism using a photoacoustic effect has been studied and developed. The photoacoustic imaging apparatus applies pulsed laser light with a narrow time width (laser pulses) into a living organism and generates an image from ultrasonic waves (photoacoustic waves) that the biological tissue generates during volume expansion due to heat generated when absorbing the energy of the pulsed laser light.

The photoacoustic imaging apparatus are under study and development as an apparatus for observing human breasts to find breast cancer in early stages. Specific configuration example is disclosed in PTL 1.

PTL 2 discloses a photoacoustic imaging apparatus including a detector in which a plurality of transducers are disposed on a container whose subject-side surface is spherical and a holding member shaped to the subject. PTL 3 also discloses a photoacoustic breast scanner including a detector in which a plurality of transducers are disposed on a curved container.

CITATION LIST

Patent Literature

PTL 1: Japanese Patent Laid-Open No. 2012-179348
PTL 2: U.S. Patent Application Publication No. 2011/306865
PTL 3: Japanese Patent No. 4341987

SUMMARY OF INVENTION

Technical Problem

Observation targets in breast cancer diagnosis are generally breasts and what-is-called axillae at the armpits (see FIG. 4). When acoustic waves are to be received, with a breast drooped into a recess of the apparatus, the nipple and its outskirt of the breast can be inserted relatively easily, but an area close to the chest wall and the axilla are not deformed so much due to gravity that it is difficult to insert. Thus, to observe the axilla, an apparatus capable of receiving acoustic waves at the shallowest possible portion of the recess, that is the boundary between a subject holding member and a base, is provided.

However, in known apparatuses, a space between the receiver and the base cannot be filled with matching liquid (an acoustic matching material) because the apparatus would become soiled or broken due to if the matching liquid spills. That is, a path from an acoustic wave generation source to the detector has a portion containing no acoustic matching material, where acoustic waves are not propagated, so that no subject information can be obtained.

For example, the apparatus disclosed in PTL 1 has an area having no acoustic matching material between the subject and an edge of the detector, or a shallow portion of the recess, so that a portion in which subject information cannot be obtained (a blind area) is generated.

Solution to Problem

The present invention provides a subject-information acquisition apparatus including a base; a subject holding member on the base; a receiver including a plurality of transducers and a support member on which the plurality of transducers are disposed; and a fluid-level adjusting mechanism configured in such a manner that an acoustic matching material in a space enclosed by the base, the subject holding member, and the receiver can be at a fluid level higher than a boundary between the subject holding member and the base.

Further features of the present invention will become apparent from the following description of exemplary embodiments with reference to the attached drawings.

Advantageous Effects of Invention

According to some embodiments of the present e from h no subject information is obtained (a blind area) can be reduced. For example, since the acoustic matching material can be kept in the vicinity of the chest wall, acoustic waves from the vicinity of the chest wall and the axillary cavity can be received and image.

BRIEF DESCRIPTION OF DRAWINGS

FIG. 1 is a block diagram of a photoacoustic-wave measurement apparatus according to an embodiment of the present invention.

FIG. 2 is a conceptual diagram of the photoacoustic-image measurement apparatus.

FIG. 3 is a diagram showing an example of a fluid circulation system of the photoacoustic-wave measurement apparatus.

FIG. 4 is a diagram illustrating a breast and an axillary cavity

FIG. 5A is a diagram illustrating a configuration of a first embodiment

FIG. 5B is a diagram illustrating the configuration of the first embodiment.

FIG. 6A is a diagram illustrating a configuration of the first embodiment.

FIG. 6B is a diagram illustrating the configuration of the first embodiment.

FIG. 7A is a diagram illustrating a configuration of a second embodiment.

FIG. 7B is a diagram illustrating the configuration of the second embodiment.

FIG. 8A is a diagram illustrating a configuration of the second embodiment.

FIG. 8B is a diagram illustrating the configuration of the second embodiment.

FIG. 9A is a diagram illustrating an example of the shape of a seal support member according to the second embodiment.

FIG. 9B is a diagram illustrating an example of the shape of the seal support member according to the second embodiment.

FIG. 10A is a diagram illustrating a configuration of a third embodiment.

FIG. 10B is a diagram illustrating the configuration of the third embodiment.

FIG. 10C is a diagram illustrating the configuration of the third embodiment.

FIG. 11A is a diagram illustrating an alignment of a receiver in a vertical direction.

FIG. 11B is a diagram illustrating an alignment of the receiver in a vertical direction.

FIG. 12A is a diagram illustrating a configuration of a fourth embodiment.

FIG. 12B is a diagram illustrating the configuration of the fourth embodiment.

FIG. 13 is a diagram illustrating a configuration of the first embodiment.

DESCRIPTION OF EMBODIMENTS

Embodiments of the present invention will be described hereinbelow with reference to the drawings. However, it is to be understood the present invention is not limited thereto without departing the scope of the present invention.

A subject-information acquisition apparatus that includes an acoustic matching material (matching liquid) between a subject and a receiver that receives acoustic waves from the subject sometimes has no acoustic matching material in a path from the subject to the receiver. In this case, the acoustic waves do not propagate, and no subject information can be obtained. Thus, a configuration in which the interface of the acoustic matching member can be higher than any paths from the subject to the transducers of the receiver allows the subject-information acquisition apparatus to receive the acoustic waves from the subject with the transducers of the receiver more reliably. That is, the blind area can be reduced. This allows subject information to be obtained more accurately.

Accordingly, a subject-information acquisition apparatus according to an embodiment of the present invention includes a base; a subject holding member on the base; a receiver including a support member on which a plurality of transducers are provided; and a fluid-level adjusting mechanism for an audio matching material. The mechanism is configured in such a manner that the top of the acoustic matching material in a space enclosed by the base, the subject holding member, the receiver, and the support member can be at a fluid level higher than a boundary between the subject holding member and the base.

Specifically, the supply and discharge of the acoustic matching member into/from the support member of the receiver may be adjusted so that the fluid level of the acoustic matching member is kept higher than the boundary between the subject holding member and the base. An area in which the acoustic matching member is provided may be tightly sealed so that the fluid level of the acoustic matching member is kept higher than the boundary between the subject holding member and the base. Embodiments of the present invention will be described hereinbelow using specific examples of the fluid-level adjusting mechanism for the acoustic matching material.

The examples in which the fluid level of the acoustic matching material is adjusted to be higher than the boundary between the subject holding member and the base so as to obtain all the acoustic waves from the subject holding member are given for illustration and are not intended to limit the present invention. The fluid-level adjusting mechanism for the acoustic matching material may be configured so that the fluid level of the acoustic matching material is higher than the position of the target subject.

First Embodiment

FIG. 1 is a block diagram of a photoacoustic-wave measurement apparatus according to an embodiment of the present invention.

The testee lies face down on a base 1 (for example, a bed), and the breast is drooped into contact with a subject holding member 11 through a breast insertion port 13, which is an opening of the base 1. The photoacoustic-wave measurement apparatus according to an embodiment of the present invention includes subject holding members 11 of a plurality of sizes depending on the size of the breast. Since subject holding members 11 of a plurality of shapes and sizes are available, generation of the clearance between the breast and the subject holding member 11 can be reduced.

The space between a measurement unit 3 (described later) and the subject holding member 11 is filled with an acoustic matching material 35 (matching liquid). Light energy is emitted from a light source 5 (described later) to a breast held by the subject holding member 11. The measurement unit 3 receives ultrasonic waves generated from the breast through the acoustic matching material 35. The intensity of the emitted light, the timing of emission of the light and reception of the acoustic waves, the scanning of a receiver (described later), and so on are controlled by a control unit 2. The received acoustic waves are converted to digital data (photoacoustic data) (analog-to-digital conversion) by a signal processing unit 4. An image generating unit 6 generates a two-dimensional or three-dimensional photoacoustic image using the photoacoustic data.

The generated photoacoustic image and an image acquired by a camera 33 are displayed on a display 7.

This embodiment shows an example in which a mechanism for adjusting the fluid level of the acoustic matching material 35 is configured to keep the level of the acoustic matching material 35 higher than the boundary between the subject holding member 11 and the base 1 by supplying and discharging the acoustic matching material 35 all the time. This reduces interruption of acoustic waves generated from the subject (in this embodiment, a breast) and passing through the subject holding member 11 by the air and so on between the subject holding member 11 and the receiver 32, thus allowing a larger amount of acoustic waves to be received by the receiver.

Subject Holding Member

The subject holding member 11 may have a first portion which is a recessed portion, for example, a bowl-shaped portion to make it easy to hold the breast. The first portion of the subject holding member 11 does not need to have a perfect spherical shape; it may have a shape corresponding to the breast and the axillary cavity. The subject holding member 11 may have a plurality of sizes depending on the size of the breast.

The subject holding member 11 can be replaced depending on the size of the breast and may have a flange-shaped second portion around the bowl-shaped portion to be fluid-tightly mounted to the base 1. A portion where the bowl-shaped first portion and the flange-shaped second portion are joined is smoothed to prevent the testee from becoming painful even in contact therewith.

An example method for mounting the second portion to the base 1 is placing a ring-shaped sealing material between the base 1 and the second portion and screwing it. If the intensity is insufficient, such as a resin second portion, the sealing material and the second portion may be reinforced with a ring-shaped metal member so as to be retained from above.

The subject holding member 11 may be a thin (0.1 mm to 0.5 mm) transparent member that allows light to pass through so that ultrasonic waves can easily pass through and that has intensity to withstand the weight of the testee. A material for the subject holding member 11 having such properties may be polyethylene terephthalate (PET). The space between the subject holding member 11 and the subject (breast) is filled with an acoustic matching material 12 so that ultrasonic waves can easily pass therethrough. Examples of the acoustic matching material 12 include water and gel.

The measurement unit 3 adjusts the position of the receiver 32 in the Z-direction depending on the size of the subject holding member 11 and moves the receiver 32 in two dimensions or three dimensions at a position where a sensitivity of the receiver is high. Scanning the highest sensitivity region of the receiver 32 at the subject is performed to obtain a good acoustic image. For that purpose, the size of the subject holding member 11 needs to be determined with the measurement unit 3.

Thus, by forming marks (for example, notches) in the subject holding member 11 for determining the size of the subject holding member 11, the measurement unit 3 can automatically determine the size using a detection unit (not shown) provided at the measurement unit 3. Examples of the detection unit include a switch and a sensor.

Alternatively, a barcode or the like may be provided on the subject holding member 11, and the kind of the subject holding member 11 may be determined using an image of the barcode acquired by the camera 33. The automatic determination of the kind of the subject holding member 11 saves manual input operation and eliminates failure due to a typing error.

Light Source

When light energy is supplied from the light source 5 to the subject, the subject generates photoacoustic waves. If the subject is a living organism, the light source 5 emits light of a specific wavelength that is absorbed by a specific component of the breast. The light source 5 may either be combined with the photoacoustic apparatus of this embodiment or be separated from the photoacoustic apparatus.

An example of the light source 5 is a pulsed light source capable of generating pulsed light of the order of a few nanoseconds to a few hundred nanoseconds. Specifically, pulse widths of about 10 to 100 nanoseconds are used to efficiently generate photoacoustic waves. A laser light source may be used because high output can be obtained, while a light-emitting diode may also be used instead of the laser. Examples of the laser may include a solid-state laser, a gas laser, a fiber laser, a dye laser, a semiconductor laser, and other various lasers. The emission timing, waveform, and intensity are controlled by a light-source control unit (not shown).

In some embodiment of the present invention, a light source used may have a wavelength that allows light to propagate into the breast. Specifically, a light source capable of generating light of wavelengths of 500 nm or more and 1,200 nm or less is preferable.

Configuration of Measurement Unit

FIG. 2 is a conceptual diagram of a measurement unit according to an embodiment the present invention. The measurement unit includes a light irradiation unit 31 that irradiates the breast with laser light guided from the light source 5 using a light guide unit 51 and at least two transducers 321 that receive ultrasonic waves generated from the breast. The measurement unit further includes the camera 33 for observing a breast holding state and a moving mechanism 34 for moving the light irradiation unit 31 in two dimensions in an X-Y plane.

The light irradiation unit 31 is disposed at a position facing the subject (breast) so as to irradiate the breast with the laser light. The transducers 321 are configured to be able to receive the acoustic waves generated from the subject. The photoacoustic waves generated due to thermal expansion of the subject irradiated with laser light are received by the receiver 32 including the plurality of transducers 321.

The space between the receiver 32 and the subject holding member 11 is filled with the acoustic matching material 35. The receiver 32 includes a support member 36 filled with the acoustic matching material 35 and including the transducers 321. An example of the acoustic matching material 35 is water or the like whose acoustic impedance is closer to a human organism than air.

The receiver 32 includes the plurality of transducers 321 that receive acoustic waves and the support member 36 (a transducer support member) on which the plurality of transducers are disposed. The plurality of transducers are disposed on the support member 36 so that a first direction in which the receiver sensitivity of part of the transducers is high differs from a second direction in which the receiver sensitivity of the other of the transducers is high and that the first direction points to one area. The one area is an area in which the plurality of transducers can receive acoustic waves generated from the one area at higher sensitivity than that when the first and second directions in which the receiver sensitivity is high are parallel, in the case where the first and second directions in which the receiver sensitivity of the plurality of transducer is high point to the one area.

This can increase the resolution of an image of the one area formed on the basis of the acoustic waves generated from the one area as compared with a case in which the first and second directions in which the receiver sensitivity of the plurality of transducers is high are parallel.

Thus, the plurality of transducers 321 may include a first transducer and a second transducer disposed on the support member 36 so that at least directions in which receiver sensitivity is high differ from each other (the directions are not parallel) and point to the one area.

The plurality of transducers may include a first transducer and a second transducer disposed on the support member 36 so that at least directions in which receiver sensitivity is the highest differ from each other and point to the one area. That is, the plurality of transducers may be disposed on the support member 36 so that a first direction in which the receiver sensitivity of part of the transducers is the highest differs from a second direction in which the receiver sensitivity of the other transducer is the highest and that the first direction points to the one area. The one area is an area in which the plurality of transducers can receive acoustic waves generated from the one area at higher sensitivity than that when the first and second directions in which the receiver sensitivity is the highest are parallel, in the case where the first and second directions in which the receiver sensitivity of the plurality of transducer is the highest point to the one area.

This disposition of the plurality transducers can further increase the receiver sensitivity of the receiver 32 to acoustic waves generated from the one area. Furthermore, this can further increase the resolution of an image of the one area formed on the basis of the acoustic waves generated from the one area as compared with a case in which the first and second directions in which the receiver sensitivity of the plurality of transducers is the highest are parallel.

Pointing the plurality of transducers whose receiver sensitivity is higher than a predetermined level to one area can increase the resolution of an image of the area. In this specification, the area capable of receiving acoustic waves at high sensitivity is referred to as a high-sensitivity area, which results in a high-resolution area. In this specification, the high-resolution area is an area of the highest resolution to half of the highest resolution. Specifically, diameter r in the following expression (1) is the diameter of the high-resolution area:

[Math. 1]

$$r = \frac{r_0}{\phi_d} \cdot \sqrt{(R^2 - R_H^2)} \quad (1)$$

where R is an allowable resolution, $R_H$ is the highest resolution, $r_0$ is the diameter of a sphere on which the transducers 321 are disposed, and $\Phi_d$ is the diameter of a first transducer 321. In this specification, the allowable resolution R is half of the highest resolution $R_H$.

The moving mechanism 34 may be either a biaxial moving mechanism capable of scanning in the X-Y direction or a triaxial moving mechanism capable of three-dimensional scanning in XYZ-directions. The biaxial moving mechanism or the triaxial moving mechanism can be constituted by, for example, a stage, a linear guide, a feed-screw mechanism (not shown), and a motor (not shown).

Transducer

The transducers 321 detect acoustic waves and convert it to electrical signals or analog signals. Any transducers capable of detecting acoustic waves, such as a transducer using a piezoelectric phenomenon, a transducer using the resonance of light, and a transducer using a change in capacitance. In this embodiment, the transducers 321 are disposed in a plurality of positions so that the directions in which the receiver sensitivity is the highest differ from one another. Using such multidimensional array transducers allows acoustic waves to be detected at a plurality of locations at the same time, thus reducing the detection time.

Receiver

The support member 36 is a member that supports the plurality of transducers 321. The support member 36 may have a shape that allows the plurality of transducers 321 to be disposed. That is, the support member 36 may support the plurality of transducers 321 so that the plurality of transducers 321 are disposed on a closed curve surrounding the breast in view of the receiver sensitivity to the acoustic waves. For example, when the plurality of transducers 321 are disposed on the spherical surface so that directions (directivity) in which the receiver sensitivity of the plurality of transducers 321 is the highest point to the center of the sphere, the receiver sensitivity at the center of the receiver 32 is the highest. However, it is difficult to dispose the plurality of transducers 321 on the entire closed curve surrounding the subject (breast).

Thus, for example, the support member 36 may have a first portion or a recessed portion and a second portion extending upwardly from the first portion. The second portion is located periphery of the first portion and outwardly extending from the first portion such that the acoustic matching fluid is stored enough between the support member 36 and the receiver 32 located beneath the support member 36. The plurality of transducers 321 may be disposed along the recessed surface of the first portion.

The recessed surface may either be a curved surface or be composed of a plurality of flat surfaces. The recessed surface (if the recessed surface is composed of a plurality of flat surfaces, an approximate curved surface) may be a curved surface whose center of curvature is located in the one area (the high-sensitivity area). In the case where the plurality of transducers 321 are disposed along the curved surface, the curved surface may have a shape so that directions in which the receiver sensitivity of at least part of the plurality of transducers 321 is the highest intersect. Furthermore, the recessed surface may have a shape so that an angle formed by surfaces perpendicular to the directions in which the receiver sensitivity of adjacent transducers 321 of the plurality of transducers 321 is the highest is larger than 0 degree and smaller than 180 degrees.

Such a shape of the recessed surface of the support member 36 causes the directions in which the receiver sensitivity of the plurality of transducers 321 disposed on the support member 36 is the highest to converge in the one specific area, thus achieving the high receiver sensitivity of the receiver 32 to acoustic waves generated from the one area.

Specifically, the support member 36 has a spherical surface, and the plurality of transducers 321 can be arranged along the spherical surface. Here, the spherical surface includes spherical surfaces other than a true spherical surface. That is, the spherical surface includes a spherical surface having an opening, such as a hemispherical surface. The spherical surface further includes a surface having surface irregularities that can be regarded as a spherical surface and an ellipsoidal surface that can be regarded as a spherical surface (an ellipsoid expanded in three dimensions, whose surface is formed of a surface of the second order).

The support member 36 may have a shape such that directions in which the receiver sensitivity of the plurality of transducers 321 provided on the support member 36 is the highest point to one area in the subject. The one area is an area in which the receiver sensitivity of the receiver 32 to acoustic waves generated from the one area is higher than that when the plurality of transducers 321 are disposed in parallel, as described above. In the case where the subject-information acquisition apparatus includes the subject holding member 11, the shape of the support member 36 and the disposition of the plurality of transducers 321 may be set so that the one area can be located in the subject insertion area of the subject holding member 11 during reception of acoustic waves.

As in this embodiment, the plurality of transducers 321 may be disposed on the support member 36 so that the receiving surfaces of the plurality of transducers 321 are disposed inside the hemispherical support member 36. The hemispherical shape includes not only an exact hemisphere is but also a partially cutout sphere. The sphere includes not only a true sphere but also a surface having surface irregularities that can be regarded as a spherical surface and an ellipsoidal surface that can be regarded as a spherical surface (an ellipsoid expanded in three dimensions, whose surface is formed of a surface of the second order).

The plurality of transducers 321 may be disposed on the support member 36 so that they can be sampled at regular intervals in k-space. Data in k-space is Fourier transform of data in real space. That is, the coordinates in real space is positon coordinates (x, y, z), and k-space (kx, ky, kz) is in spatial frequency domain. For example, the plurality of transducers 321 may be disposed in a spiral, as disclosed in PTL-1. The support member 36 may have any shape provided that the plurality of transducers 321 can be disposed so as to form a desired high-resolution area.

The support member 36 is configured so that the level of the acoustic matching material 35 between the subject holding member 11 and the receiver 32 is higher than the boundary between the subject holding member 11 and the base 1. The support member 36 has a shape that allows the level of the acoustic matching material 35 to be kept higher than the boundary between the subject holding member 11 and the base 1 even if the receiver 32 scans in the X-Y direction. Thus, the support member 36 of this embodiment is formed of the hemispherical first portion on which the transducers 321 are disposed and the second portion extending therefrom toward the outer periphery, as shown in FIG. 2. The support member 36 may be formed of either one component or a plurality of components.

The support member 36 may further include the light irradiation unit 31. This allows the relationship between an acoustic-wave detection position and a light irradiation position to be kept constant, thus allowing more uniform photoacoustic wave information to be acquired.

A breast irradiation area is limited by the American National Standards Institute (ANSI) standard. Thus, the irradiated area is limited in view of the cost of the light source 5, although the irradiation intensity and irradiation area may be increased to increase the amount of light propagated into the breast. Even if an area having low detection sensitivity is irradiated with light, its light use efficiency is low because of the directivity of the transducers 321. Therefore, irradiating the whole of the breast with light is inefficient. That is, applying light only to an area having high sensitivity to the receiver 32 formed of the plurality of transducers 321 is efficient. Thus, the light irradiation unit 31 may be moved together with the receiver 32.

Light Guide Unit

The light emitted from the light source 5 in FIG. 1 is guided to the subject while being processed into desired light distribution by a light guide unit 51 (optical components, typically, lenses and mirrors). The light can be propagated through an optical waveguide, such as an optical fiber, a bundle of optical fibers, or an articulating arm in which a mirror or the like is combined with a lens-barrel. They are also included in the light guide unit 51. Other examples of the light guide unit 51 include a mirror that reflects light, a lens that changes the shape of light, such as collecting or expanding light, and a diffuser that diffuses light.

Any optical components may be used provided that they irradiate the breast with the light generated from the light source 5 into a desired shape. The light may be expanded to a certain area rather than being collected by lenses in view of increasing a subject diagnoses area. In the case where desired pulsed light can be directly emitted from the light source 5 to the breast and can be scanned together with the support member 36, the photoacoustic apparatus may not include the light guide unit 51.

Fluid Circulation System

FIG. 3 is a diagram showing an example of a fluid circulation system 8 according to an embodiment of the present invention. The fluid circulation system 8 includes a pump 81, a tank 82, a channel switching unit 83, a purification unit 84, a defoaming (deaerating) unit 85, a warming unit 86, flowmeters 87a and 87b, pipes 80a and 80b, and a fluid level sensor 88 and has the following configurations.

The acoustic matching material 35 is reserved in the tank 82 and is fed to the purification unit 84 that purifies the acoustic matching material 35 by the pump 81 via the channel switching unit 83. The purified acoustic matching material 35 is supplied to the support member 36 via the defoaming (deaerating) unit 85 that removes air and bubbles melted in the acoustic matching material 35 and the warming unit 86 that warms the acoustic matching material 35 through the pipe 80a. The amount and flow rate of the acoustic matching material 35 supplied to the support member 36 are measured and controlled by the flowmeter 87a.

Whether the acoustic matching material 35 supplied to the support member 36 is kept at a sufficient level is checked by the fluid level sensor 88. If the level falls, a measurement error or warning can be displayed on the display 7. The acoustic matching material 35 supplied to the support member 36 is discharged through the pipe 80b via a fluid-level adjusting mechanism 9 for the acoustic matching material 35 (described later). The amount of the acoustic matching material 35 discharged through the pipe 80b is measured by the flowmeter 87b, so that whether the acoustic matching material 35 fins the support member 36 and circulates therethrough can be checked.

The pump 81 may be disposed at a plurality of locations, such as when the acoustic matching material 35 has to be discharged while being supplied. Any kind of pump may be used provided that it can circulate the acoustic matching material 35. A gear pump or a tube pump can make the acoustic matching material 35 flow in both directions of supply and discharge by reversing the rotation of the motor, thus reducing the frequency of switching of the channel switching unit 83. The channel switching unit 83 can be combined with an electromagnetic valve or the like and allows switching between a pipe for feeding the acoustic matching material 35 to the pump 81 and a pipe for discharging the acoustic matching material 35 from the 81 pipe.

An example of the purification unit 84 is a filtration unit, which purifies the acoustic matching material 35 to prevent contamination thereof.

Since bubbles in the acoustic matching material 35 would affect reception of acoustic waves, the bubbles and melted gas are removed from the acoustic matching material 35 by the defoaming (deaerating) unit 85.

The defoaming (deaerating) unit 85 is connected to the warming unit 86. The defoamed (deaerated) acoustic matching material 35 is sent to the warming unit 86. If the acoustic matching material 35 is excessively cold, the testee feels uncomfortable, so that the acoustic matching material 35 is warmed to nearly a body temperature by the warming unit 86. The warming unit 86 is configured to keep the acoustic matching material 35 at a constant temperature because a change in the temperature of the acoustic matching material 35 will change the velocity of sound, thus affecting the received sound waves.

The tank 82 has a capacity capable of reserving all the acoustic matching material 35 flowing through the support member 36 and the fluid circulation system 8 and includes a supply port and a discharge port (not shown). The purification unit 84, the defoaming (deaerating) unit 85, and the warming unit 86 may be disposed in the tank 82. The pump 81, the tank 82, the channel switching unit 83, the purification unit 84, the defoaming (deaerating) unit 85, and the warming unit 86 may be omitted or changed in the order of connection for optimization, Fluid-Level Adjusting Mechanism for Acoustic Matching Material FIGS. 5A and 5B are diagrams illustrating an example of the fluid-level adjusting mechanism 9 for the acoustic matching material 35 according to an embodiment of the present invention. The fluid-level adjusting mechanism 9 includes a side wall provided at the second portion of the support member 36, a sealing material 911, a fluidproof-film attaching portion 912, a fluidproof film 913, and an acoustic-matching-material collection pan 914, which is an acoustic-matching-material collection groove.

FIG. 5A shows a case in which the center of the receiver 32 and the center of the subject are aligned, and FIG. 5B shows a case in which the receiver 32 is moved for scanning. Providing the side wall at the end of the second portion of the support member 36 allows an area higher than the top of the first portion and enclosed by the side wall to be filled with the acoustic matching material 35 in the support member 36. This allows the fluid level of the acoustic matching material 35 to be higher than that of a case in which the support member 36 has only the first portion, thus reducing portion in which the acoustic matching material 35 is not present in the path from the subject to the transducer 32.

The side wall at the end of the second portion of the support member 36 is provided with the sealing material 911. The sealing material 911 can extend and contract in the Z-direction and is in slidable contact with the base 1. The sealing material 911 has a role in reducing the amount of the acoustic matching material 35 discharged from the support member 36. Furthermore, a change in the distance between the support member 36 and the base 1 when the receiver 32 is moved in the Z-direction can be absorbed using deformation of the sealing material 911.

Next, a method for circulating the acoustic matching material 35 will be described. The acoustic matching material 35 is supplied to the support member 36 in an empty state through the pipe 80a. The acoustic matching material 35 supplied to the lower limit of a measurable level can be sensed by the fluid level sensor 88 (shown in FIG. 3). The acoustic matching material 35 further continues to be supplied through the pipe 80a, overflows from between the sealing material 911 and the base 1, flows along the side of the support member 36, and is collected in the acoustic-matching-material collection pan 914 provided around the outer periphery of the second portion.

When the support member 36 scans, the acoustic matching material 35 drops or flows from the base 1. Thus, the fluidproof film 913 is attached to the fluidproof-film attaching portion 912 of the base 1, so that the acoustic matching material 35 is collected into the acoustic-matching-material collection pan 914 also through a path along the fluidproof film 913. The fluidproof film 913 is provided between the fluidproof-film attaching portion 912 and the acoustic-matching-material collection pan 914 to connect them. The fluidproof film 913 is made of a material that does not allow the acoustic matching material 35 to pass therethrough and has elasticity or is disposed with slack so as not to hinder scanning even if it is drawn during scanning.

The amount of the acoustic matching material 35 supplied from the fluid circulation system 8 is measured by the flowmeter 87a shown in FIG. 3), so that the acoustic matching material 35 can be supplied at a flow rate at which the fluid level in the support member 36 does not decrease. The acoustic matching material 35 collected in the acoustic-matching-material collection pan 914 circulates through the apparatus in such a manner that it passes through the pipe 80b, is purified, deaerated, and warmed in the fluid circulation system 8, and is again supplied through the pipe 80a at a constant temperature and flow rate.

As shown in FIGS. 6A and 6B, the configuration of the acoustic-matching-material collection pan 914 and the fluidproof-film attaching portion 912 may be opposite to that in FIGS. 5A and 5B. That is, the acoustic-matching-material collection pan 914 may be mounted to the base 1 so as to enclose the receiver scanning area, and the acoustic-matching-material collection pan 914 and the support member 36 may be connected together using the fluidproof film 913.

The configuration of this embodiment in which the acoustic matching material 35 circulates in the subject-information acquisition apparatus is given for illustration and is not intended to limit the present invention. The subject-information acquisition apparatus may have a configuration in which the acoustic matching material 35 does not circulate in the apparatus provided that the level of the acoustic matching material 35 is higher than a necessary level (for example, the acoustic matching material 35 continues to overflow).

With the above configuration, the acoustic matching material 35 is kept full to a position in contact with the base 1. Thus, the periphery of the subject holding member 11 is filled with the acoustic matching material 35, this allows acoustic waves from not only the periphery of the nipple of the breast but also the vicinity of the chest wall and the axillary cavity to be received and imaged.

Although the base 1 shown in FIGS. 5A and 5B and FIGS. 6A and 6B has a recess opposite to the receiver 32, the base 1 may be flat as shown in FIG. 13. The shape in which the side opposite the receiver 32, that is, the subject insertion side, is recessed makes it easy to insert the breast into the subject holding member 11, thus reducing the burden on the testee and allowing acoustic waves from the vicinity of the chest wall and the axillary cavity to be received and imaged.

Second Embodiment

FIGS. 7A and 7B are diagrams showing a fluid-level adjusting mechanism 9 for the acoustic matching material 35 according to a second embodiment of the present invention. In this embodiment, differences from the first embodiment will be specifically described. The fluid-level adjusting mechanism 9 of this embodiment includes an elastic sealing material 921.

FIG. 7A shows a case in which the center of the receiver 32 and the center of the subject are aligned, and FIG. 7B shows a case in which the receiver 32 is moved for scanning. The fluid-level adjusting mechanism 9 of this embodiment does not collect the overflowing acoustic matching material 35 as in the first embodiment but connects the support member 36 and the base 1 using the elastic sealing material 921. This allows a space enclosed by the support member 36, the base 1, the subject holding member 11, and the sealing material 921 to be tightly sealed. Thus, the acoustic matching material 35 can be at a desired level (for example, a position higher than the boundary between the subject holding member 11 and the base 1).

Next, a method for circulating the acoustic matching material 35 will be described. The acoustic matching material 35 is supplied to the support member 36 in an empty state through the pipe 80a. The acoustic matching material 35 supplied to the lower limit of a measurable level can be sensed by the fluid level sensor 88 (shown in FIG. 3). The further supplied acoustic matching material 35 is discharged through the discharge pipe 80b provided at an upper part of the space. The discharge pipe 80b is disposed at the upper part so that the air is completely let out because bubbles remaining in the support member 36 would interfere with the acoustic waves.

The sealing material 921 is made of a material that does not allow the acoustic matching material 35 to pass therethrough and has elasticity so as not to hinder scanning even if it is drawn during scanning. However, depending on the amount of the acoustic matching material 35 or the shape of the support member 36, the sealing material 921 could be drawn and deformed due to the pressure of the acoustic matching material 35, thus hindering the scanning.

In this case, using a seal support member 922, shown in FIGS. 8A and 8B, allows the sealing material 921 to be supported so as not to be deformed due to the fluid pressure and to be extended and contracted in the scanning direction of the receiver 32. For example, the seal support member 922 is disposed so as to enclose the sealing material 911 between the base 1 and the receiver 32. The seal support member 922 is configured to be extendable and contractible in a direction parallel to the scanning direction of the receiver 32 and not to be deformed in the direction of gravity or to be deformed due to a load larger than that in the horizontal direction. This configuration allows the seal support member 922 to prevent the deformation of the sealing material 921 without interfering with the scanning of the receiver 32, thus suitably supporting the sealing material 921.

An example of the seal support member 922 has a ring shape as to enclose the outer periphery of the subject holding member 11, as shown in FIGS. 9A and 9B, thus re-inforcing and supporting the sealing material 921.

The amounts of the acoustic matching material 35 supplied to and discharged from the fluid circulation system 8 are measured by the flowmeters 87a and 87b (shown in FIG. 3), respectively. The acoustic matching material 35 discharged through the discharge pipe 80b circulates through the apparatus in such a manner that it is purified, deaerated, and warmed in the fluid circulation system 8 and is again supplied through the pipe 80a at a constant temperature and flow rate.

The configuration of this embodiment in which the acoustic matching material 35 circulates in the subject-information acquisition apparatus is given for illustration and is not intended to limit the present invention. The subject-information acquisition apparatus may have a configuration in which the acoustic matching material 35 does not circulate in the apparatus provided that the fluid level of the acoustic matching material 35 is higher than a necessary level (for example, the acoustic matching material 35 continues to overflow).

Also with the configuration of this embodiment, the acoustic matching material 35 in the space tightly sealed by the support member 36, the base 1, subject holding member 11, and the sealing material 921 is at a desirable level. That is, the fluid level of the acoustic matching material 35 is higher than the boundary between the subject holding member 11 and the base 1, for example. An implemented example is that the space tightly sealed by the support member 36, the base 1, the subject holding member 11, and the sealing material 921 is filled with the acoustic matching material 35. This allows acoustic waves not only from the periphery of the nipple of the breast but also from the vicinity of the chest wall and the axillary cavity to be received and imaged.

Third Embodiment

FIGS. 10A to 10C are diagrams showing a fluid-level adjusting mechanism 9 for the acoustic matching material 35 according to a third embodiment of the present invention. In this embodiment, differences from the first and second embodiments will be specifically described.

The fluid-level adjusting mechanism 9 of this embodiment includes a peripheral wall 932 (a side wall), a partition 931, and a pipe connecting unit 933. The peripheral wall 932 is disposed along the end of the receiver 32, specifically, along the end of the second portion of the support member 36, for example. The partition 931 protrudes inside the peripheral wall 932 from the base 1 toward the receiver 32.

The pipe connecting unit 933 has an opening end at a position higher than a desired fluid level of the acoustic matching material 35 between the partition 931 and the subject holding member 11 (for example, a position higher than the boundary between the base 1 and the subject holding member 11) and is connected to the pipe 80b. The peripheral wall 932 and the partition 931 have a ring-shaped structure so as to enclose the subject holding member 11. The ring-shaped structure continues in a direction in which the subject holding member 11 is enclosed.

FIG. 10A shows a state in which the center of the receiver 32 and the center of the subject are aligned. The acoustic matching material 35 is supplied to the support member 36 in an empty state through the pipe 80a. The acoustic matching material 35 gradually increases in fluid level into contact with the partition 931. This forms a closed space 935 enclosed by the partition 931, the acoustic matching material 35, and the base 1. At that time, a valve 934 is open, so that the closed space 935 is at atmospheric pressure, allowing air to freely get in and out.

The fluid level can be detected by one or more fluid level sensors 88 (shown in FIG. 3). The valve 934 is closed at a position where the level of the acoustic matching material 35 is higher than the lower end of the partition 931 and lower than the upper end of the peripheral wall 932 (FIG. 10A). The fluid level of the acoustic matching material 35 in the closed space 935 can be increased by absorbing the air in the closed space 935 through the pipe connecting unit 933 and the pipe 80b with the fluid circulation system 8 to bring the closed space 935 to negative pressure.

Thereafter, the amount of the acoustic matching material 35 supplied through the pipe 80a and the amount of air discharged through the pipe 80b are brought to substantially the same. This allows the fluid level of the closed space 935 to be increased while the fluid level between the partition 931 and the peripheral wall 932 is kept substantially constant. If it is difficult to bring the amount of the acoustic matching material 35 supplied and the amount of air discharged to substantially the same, the flow rate may be controlled so that the fluid level between the partition 931 and the peripheral wall 932 is kept substantially constant by detecting the fluid level between the partition 931 and the peripheral wall 932 with a sensor or the like.

The opening end of the pipe connecting unit 933 may be disposed at an upper part of the space enclosed by the partition 931 so that the air is completely let out or alternatively may be disposed in the base 1 because bubbles remaining in the support member 36 would interfere with the acoustic waves.

After the fluid level inside the partition 931 increases to the opening end of the pipe connecting unit 933 to bring the boundary between the subject holding member 11 and the base 1 into contact with the acoustic matching material 35, as shown in FIG. 10B, the amounts of the acoustic matching material 35 supplied through the pipe 80a and discharged through the pipe 80b are brought to substantially the same amount. The discharged acoustic matching material 35 is purified, deaerated, and warmed in the fluid circulation system 8 and circulates through the apparatus at a constant temperature and flow rate. After the acoustic matching material 35 comes into contact with the boundary between the subject holding member 11 and the base 1, the supply of the acoustic matching material through the pipe 80a and the discharge through the pipe 80b may be stopped and form a tightly sealed space.

The configuration of this embodiment in which the acoustic matching material 35 circulates in the subject-information acquisition apparatus is given for illustration and is not intended to limit the present invention. The subject-information acquisition apparatus may have a configuration in which the acoustic matching material 35 does not circulate in the apparatus provided that the fluid level of the acoustic matching material 35 is higher than a necessary level (for example, the acoustic matching material 35 continues to overflow).

FIG. 10C shows a case in which the receiver 32 further scans from the state in FIG. 10B. This embodiment needs no sealing material, as in the first and second embodiments, because the closed space 935 enclosed by the partition 931, the subject holding member 11, and the base 1 can be filled with the acoustic matching material 35 by causing a negative pressure therein.

Also with the configuration of this embodiment, the fluid level of the acoustic matching material 35 is always kept higher than the boundary between the base 1 and the subject holding member 11, and the periphery of the subject holding member 11 is also filled with the acoustic matching material 35. Thus, acoustic matching is always achieved in the space between the subject holding member 11 and the receiver 32. This allows acoustic waves from not only the periphery of the nipple of the breast but also the vicinity of the chest wall and the axillary cavity to be received and imaged.

FIGS. 11A and 11B are diagrams showing an example configuration of an apparatus in which the subject holding member 11 can be replaced depending on the size of the subject. FIG. 11A shows a case in which a large subject holding member 11a is used, and FIG. 11B shows a case in which a small subject holding member 11b is used. The receiver 32 may have a highest resolution area, in which the subject is located. Thus, the position of the receiver 32 may be adjusted in the Z-direction using the moving mechanism 34 to optimize the positional relationship between the subject and the receiver 32 in the Z-direction after the subject holding member 11 is replaced.

The partition 931 and the peripheral wall 932 may be short enough in the Z-direction to prevent them from coming into contact with the support member 36 and the base 1 even if the small subject holding member 11b is used (FIG. 11B). The partition 931 and the peripheral wall 932 need to be long enough in the Z-direction so that the lower end of the partition 931 and the upper end of the peripheral wall 932 overlap even with the large subject holding member 11a (FIG. 11A), and that the fluid level can be controlled. Thus, the lengths of the partition 931 and the peripheral wall 932 in the Z-direction are set to lengths that satisfy the above conditions.

Fourth Embodiment

FIGS. 12A and 12B are diagrams showing a fluid-level adjusting mechanism 9 for the acoustic matching material 35 according to a fourth embodiment of the present invention. FIG. 12A shows a case in which the center of the receiver 32 and the center of the subject are aligned, and FIG. 12B shows a case in which the receiver 32 is moved for scanning. This embodiment has a configuration in which the overflowing acoustic matching material 35 is collected, as in the first embodiment. Differences between this embodiment and the first embodiment are that the sealing material 911 is not provided between the support member 36 and the base 1 and that a fluid level sensor 915 (described later) is provided above the fluid level sensor 88 for detecting the lower limit of the fluid level necessary for measurement. Thus, the differences from the first embodiment will be described.

A method for circulating the acoustic matching material 35 according to this embodiment will be described. The acoustic matching material 35 is supplied to the support member 36 in an empty state through the pipe 80a. The acoustic matching material 35 supplied to the lower limit of a measurable level can be sensed by the fluid level sensor 88. The acoustic matching material 35 continues to be further supplied through the pipe 80a, and is filled enough to an upper limit level which is detected by the fluid level sensor 915.

A necessary height between the fluid level sensor 915 and the fluid level sensor 88 depends on the scanning speed of the receiver 32, the viscosity and other properties of the acoustic matching material 35, the shape of the support member 36, an acoustic matching material supply speed of the fluid circulation system 8, and so on. Specifically, the difference in height between the fluid level sensor 915 and the fluid level sensor 88 may be larger than the fluid level of the acoustic matching material 35 that is temporarily decreased when the fluid level fluctuates during the scanning of the receiver 32, or when the acoustic matching material 35 overflows the support member 36. That is, the surface of the acoustic matching material 35 may be always higher than the fluid level sensor 88 during the scanning.

The acoustic matching material 35 continues to be supplied through the pipe 80a, overflowing the outer periphery of the support member 36, flowing along the side of the support member 36, and is collected in the acoustic-matching-material collection pan 914 provided around the outer periphery. As in the first embodiment, the fluidproof film 913 is attached to the fluidproof-film attaching portion 912, and thus the acoustic matching material 35 is collected in the acoustic-matching-material collection pan 914 also through the path along the fluidproof film 913. After being collected in the acoustic-matching-material collection pan 914, the acoustic matching material 35 circulates in the subject-information acquisition apparatus in such a manner that it is again supplied through the pipe 80a and the same path as that in the first embodiment.

The first embodiment has a configuration in which the space enclosed by the receiver 32, the base 1, and the subject holding member 11 is filled with the acoustic matching material 35. In contrast, this embodiment ensures that the fluid level of the acoustic matching material 35 is always higher than the fluid level detected by the fluid level sensor 88 by using the fluid level sensor 915. Thus, the fluid-level adjusting mechanism 9 of this embodiment has a configuration in which the space enclosed by the receiver 32, the base 1, the subject holding member 11, and a surface corresponding to the fluid level detected by the fluid level sensor 88 can be filled with the acoustic matching material 35.

Also with the configuration of this embodiment, the periphery of the subject holding member 11 is filled with the acoustic matching material 35. This allows acoustic waves from not only the periphery of the nipple of the breast but also the vicinity of the chest wall and the axillary cavity to be received and imaged.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-087467, filed Apr. 21, 2014, which is hereby incorporated by reference herein in its entirety.

REFERENCE SIGNS LIST 1 base
2 control unit
3 measurement unit
4 signal processing unit
5 light source
6 image generating unit
7 display
8 fluid circulation system
9 acoustic-matching-material collection structure
11 subject holding member
12 acoustic matching material
13 breast insertion port
31 light irradiation unit
32 receiver
35 acoustic matching material
36 support member

The invention claimed is:

1. A subject-information acquisition apparatus comprising:
   a bed member with an insertion opening, the bed member including an upper surface configured to be set an examinee thereon and a lower surface in opposition to the upper surface;
   a subject holding member secured to the bed member around the insertion opening configured to hold a subject inserted via the insertion opening, wherein the subject is a part of the examinee;
   a vessel located under the bed member and having an upper end configured to contain an acoustic matching liquid and establish an acoustic coupling between the acoustic matching liquid and the subject via the subject holding member;
   a receiver secured to the vessel and configured to receive an acoustic wave from the subject via the acoustic matching liquid and the subject holding member;
   a scanning unit configured to move the vessel and the receiver integrally and laterally with respect to the subject holding member; and
   a seal member secured to the upper end of the vessel and to be slidably in contact with the lower surface of the bed member,
   wherein the seal member reduces an amount of the acoustic matching liquid overflowing from the vessel during a time period of scanning.

2. The subject-information acquisition apparatus according to claim 1, wherein the subject holding member has a recessed portion protruding toward the receiver.

3. The subject-information acquisition apparatus according to claim 1, wherein the vessel includes a lower portion on which the receiver is disposed and a side wall portion extending from the lower portion toward the bed member.

4. The subject-information acquisition apparatus according to claim 3, wherein the side wall portion is located at the periphery of the lower portion and outwardly extends from the lower portion.

5. The subject-information acquisition apparatus according to claim 3, wherein the vessel has an acoustic-matching-material collection groove around an outer periphery of the side wall.

6. The subject-information acquisition apparatus according to claim 1, wherein the seal member has a deformable property.

7. The subject-information acquisition apparatus according to claim 1, further comprising an elastic sealing material elastically connecting the bed member and the vessel.

8. The subject-information acquisition apparatus according to claim 1, wherein the receiver includes a plurality of transducers disposed on the lower portion of the vessel.

9. The subject-information acquisition apparatus according to claim 1, further comprising a light irradiation portion secured to the vessel configured to irradiate the subject with a light via the subject holding member.

10. The subject-information acquisition apparatus according to claim 8,
    wherein the plurality of transducers are secured to the lower portion of the vessel in a hemispherical manner configured to gather their own sensitivity directions.

11. The subject-information acquisition apparatus according to claim 1,
    wherein the bed member and the subject holding member are located stationarily with the subject during the time period of scanning, and
    wherein the vessel and the receiver are moved together with the acoustic matching liquid with respect to the subject during the time period of scanning.

* * * * *